United States Patent
Canady et al.

(10) Patent No.: US 9,694,839 B2
(45) Date of Patent: Jul. 4, 2017

(54) MEDICAL TROLLEY CART

(71) Applicant: U.S. Patent Innovations LLC, Takoma Park, MD (US)

(72) Inventors: Jerome Canady, Lakeland, FL (US); Taisen Zhuang, Rockville, MD (US); Yan Feng, Rockville, MD (US)

(73) Assignee: U.S. Patent Innovations LLC, Takoma Park, MD (US)

( * ) Notice: Subject to any disclaimer, the term of this patent is extended or adjusted under 35 U.S.C. 154(b) by 0 days.

(21) Appl. No.: 14/876,316

(22) Filed: Oct. 6, 2015

(65) Prior Publication Data

US 2016/0095779 A1    Apr. 7, 2016

Related U.S. Application Data

(60) Provisional application No. 62/060,529, filed on Oct. 6, 2014.

(51) Int. Cl.
| | |
|---|---|
| *B62B 3/10* | (2006.01) |
| *B62B 1/26* | (2006.01) |
| *B62B 3/04* | (2006.01) |
| *A61B 50/13* | (2016.01) |
| *A61B 50/15* | (2016.01) |
| *A61B 50/18* | (2016.01) |

(52) U.S. Cl.
CPC ............... *B62B 3/04* (2013.01); *A61B 50/13* (2016.02); *A61B 50/15* (2016.02); *B62B 3/104* (2013.01); *A61B 2050/185* (2016.02)

(58) Field of Classification Search
CPC .... B62B 1/10; B62B 1/12; B62B 1/26; B62B 3/02; B62B 3/04; B62B 3/08; B62B 3/10; B62B 3/003; B62B 3/004; B62B 3/005; B62B 2202/022; B62B 2202/56; A47B 2031/006; A47B 31/00; B25H 1/04; B25H 1/12; B25H 1/18; B25H 3/00; A61G 12/001; A61B 50/10; A61B 50/20; A61B 50/30
See application file for complete search history.

(56) References Cited

U.S. PATENT DOCUMENTS

| | | | | |
|---|---|---|---|---|
| 5,630,566 | A * | 5/1997 | Case | A47B 23/046 248/122.1 |
| 5,702,115 | A * | 12/1997 | Pool | A61G 12/001 280/47.35 |
| 6,259,067 | B1 * | 7/2001 | Faries, Jr. | A61B 50/10 219/394 |
| 2010/0289236 | A1 * | 11/2010 | Bennett | B62B 3/10 280/79.11 |

* cited by examiner

*Primary Examiner* — Bryan Evans
(74) *Attorney, Agent, or Firm* — 24IP Law Group; Timothy R DeWitt

(57) ABSTRACT

A medical trolley cart having a main housing with an interior chamber. The main housing has front, back, first side, second side, top and bottom panels. A front door on the front of said main housing provides accessing an interior chamber, which may have a plurality of sliding shelves. A rear door on the rear of said main housing provides access to a rear portion of the interior chamber or to a second chamber within the cart. The rear door has a hinge around which the door is opened and a latch for holding the rear door in a closed position. The rear door opens to a maximum point at which the rear door forms an angle of 15-40 degrees with the main housing.

12 Claims, 12 Drawing Sheets

MEDICAL TROLLEY CART

CROSS-REFERENCE TO RELATED APPLICATIONS

The present application claims the benefit of the filing date of U.S. Provisional Patent Application Ser. No. 62/060,529 filed by the present inventors on Oct. 6, 2014.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to medical trolley carts and, more specifically, medical trolley carts for use with electrosurgical and argon plasma coagulation systems.

Brief Description of the Related Art

Operating rooms typically have many different types of equipment that can be used in many different types of surgery. The equipment often includes various monitors, electrosurgical generators, plasma systems and gas tanks. These various types of equipment are commonly stored on multiple carts or trolleys to allow operating room personal to move the equipment being used for a particular surgical procedure into a convenient positions and to move equipment not be used out of the way of the operating room personnel.

SUMMARY OF THE INVENTION

In a preferred embodiment, the present invention is a medical trolley cart that provides a means for housing, moving and using a variety of equipment that may be needed for a particular surgical procedure in one convenient unit.

In a preferred embodiment, the present invention is a medical trolley cart. The medical trolley cart comprises a main housing having an interior chamber. The main housing has front, back, first side, second side, top and bottom panels. A front door on the front of said main housing provides accessing an interior chamber, which may have a plurality of sliding shelves. A rear door on the rear of said main housing provides access to a rear portion of the interior chamber or to a second chamber within the cart. The rear door has a hinge around which the door is opened and a latch for holding the rear door in a closed position. The rear door opens to a maximum point at which the rear door forms an angle of 15-40 degrees with the main housing. The hinge may be on the bottom of the rear door or on a side of the rear door. A plurality of gas tanks are held within the rear portion of the interior chamber and may be accesses through the rear door. The gas tanks are removably mounted to the door such that when the rear door is opened, that portions of the gas tanks having control valves extends out of the interior chamber and are accessible to operating room personally. The main housing further may have a plurality of drawers, work stations or shelves that that have retracted and extended positions such that they are within the interior chamber of the main housing when retracted.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
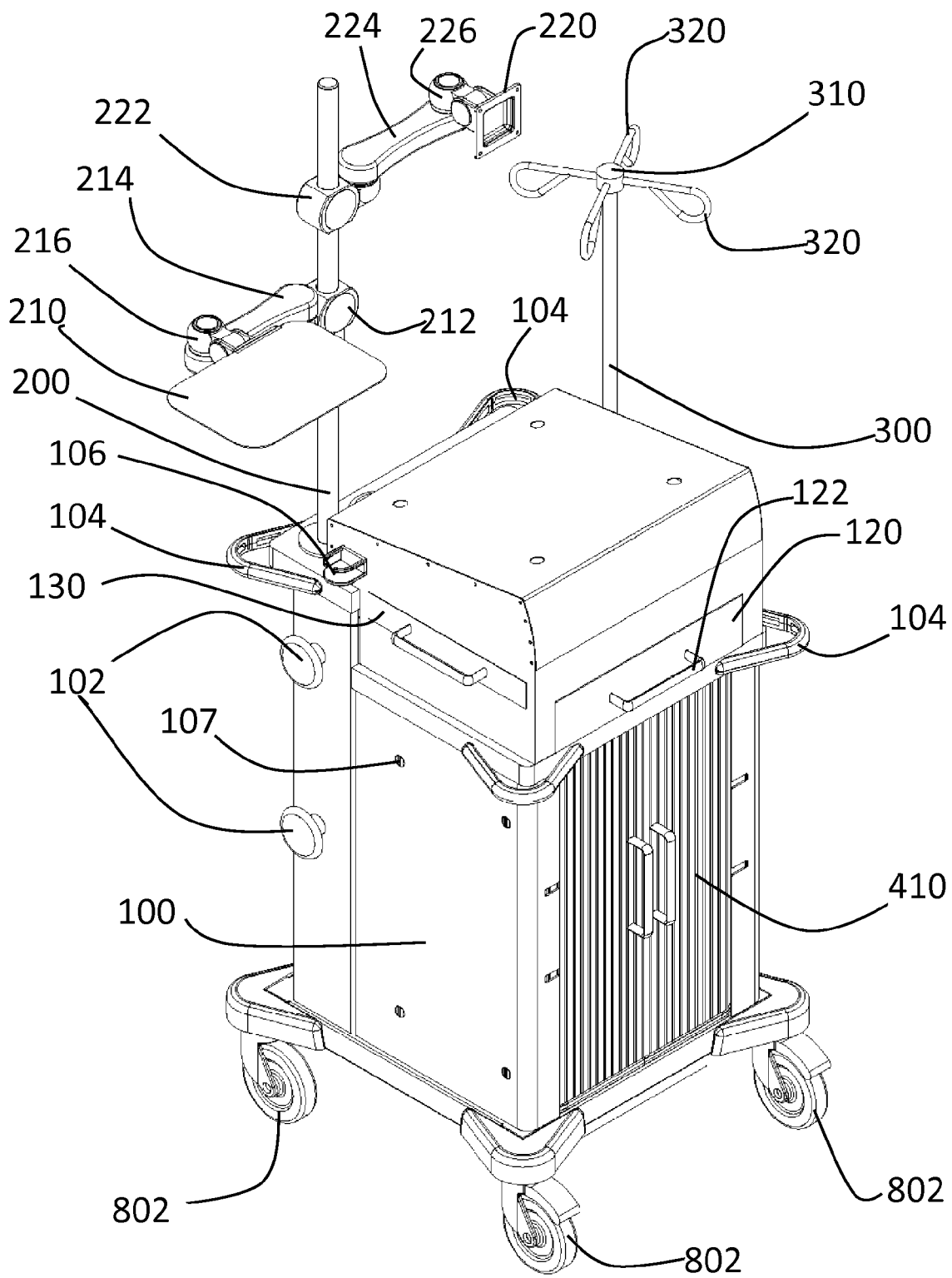
FIG. 1 is a front perspective view of a medical trolley cart in accordance with a preferred embodiment of the present invention.
Figure 2:
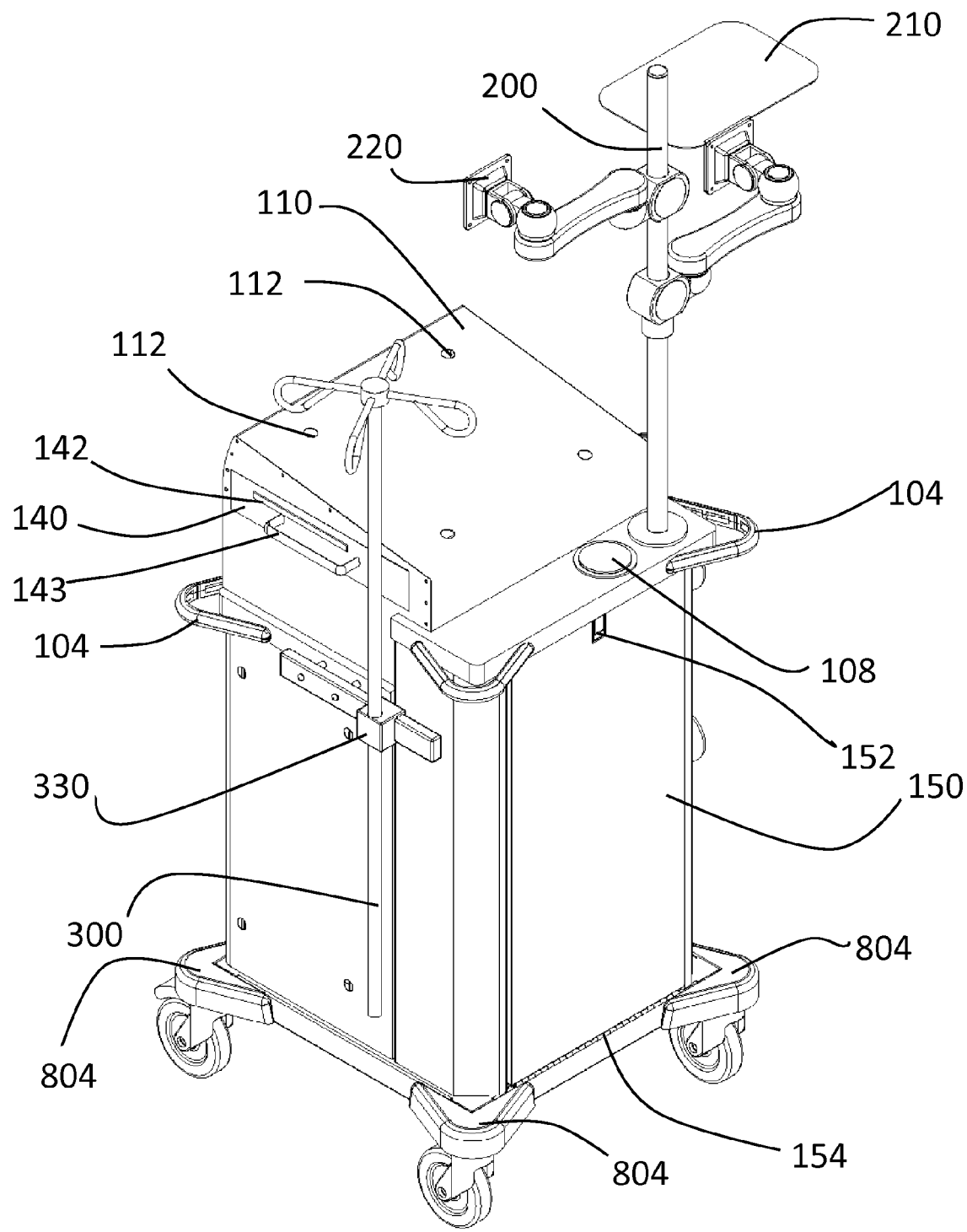
FIG. 2 is a rear perspective view of a medical trolley cart in accordance with a preferred embodiment of the present invention.
Figure 3:
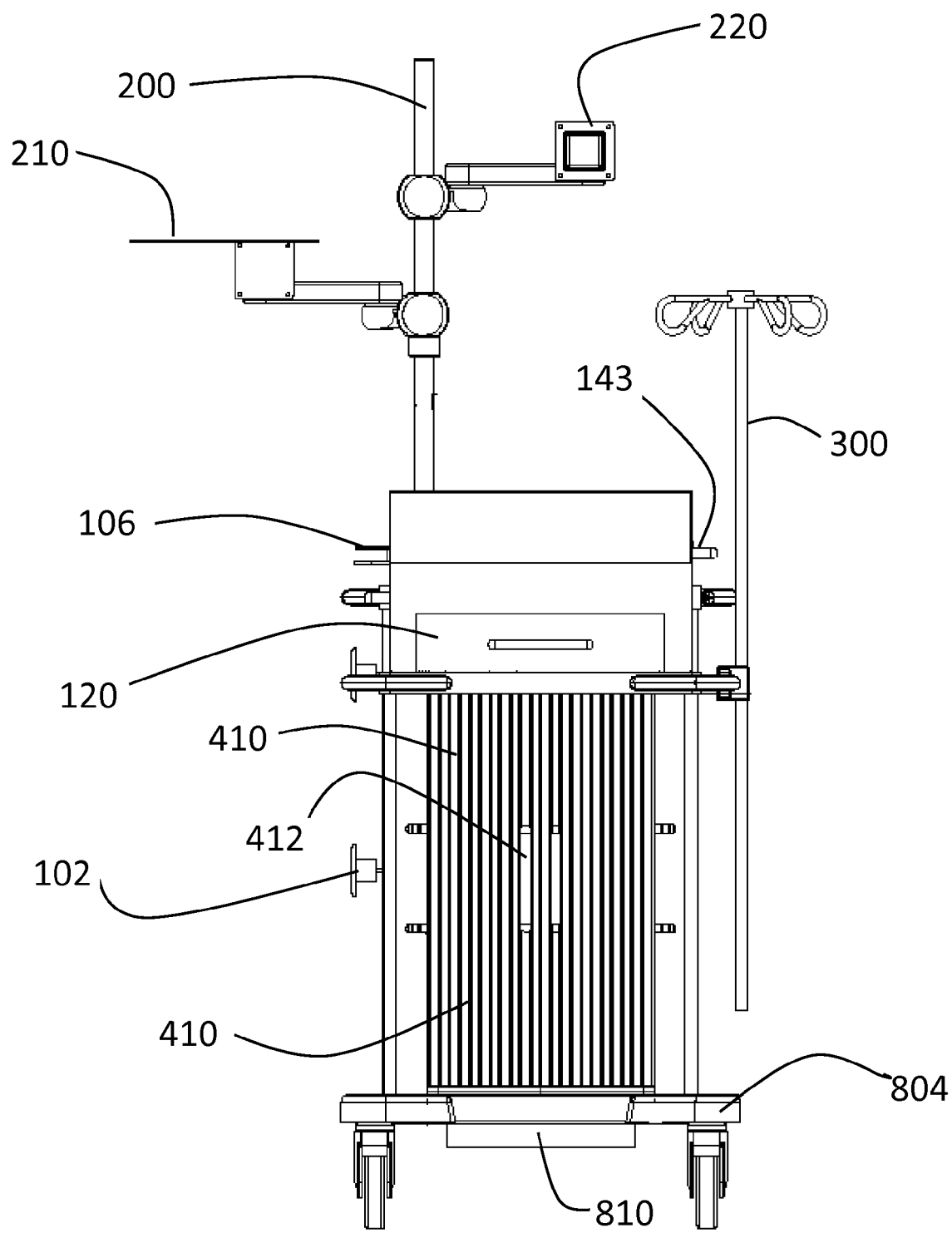
FIG. 3 is a front view of a medical trolley cart in accordance with a preferred embodiment of the present invention.
Figure 4:
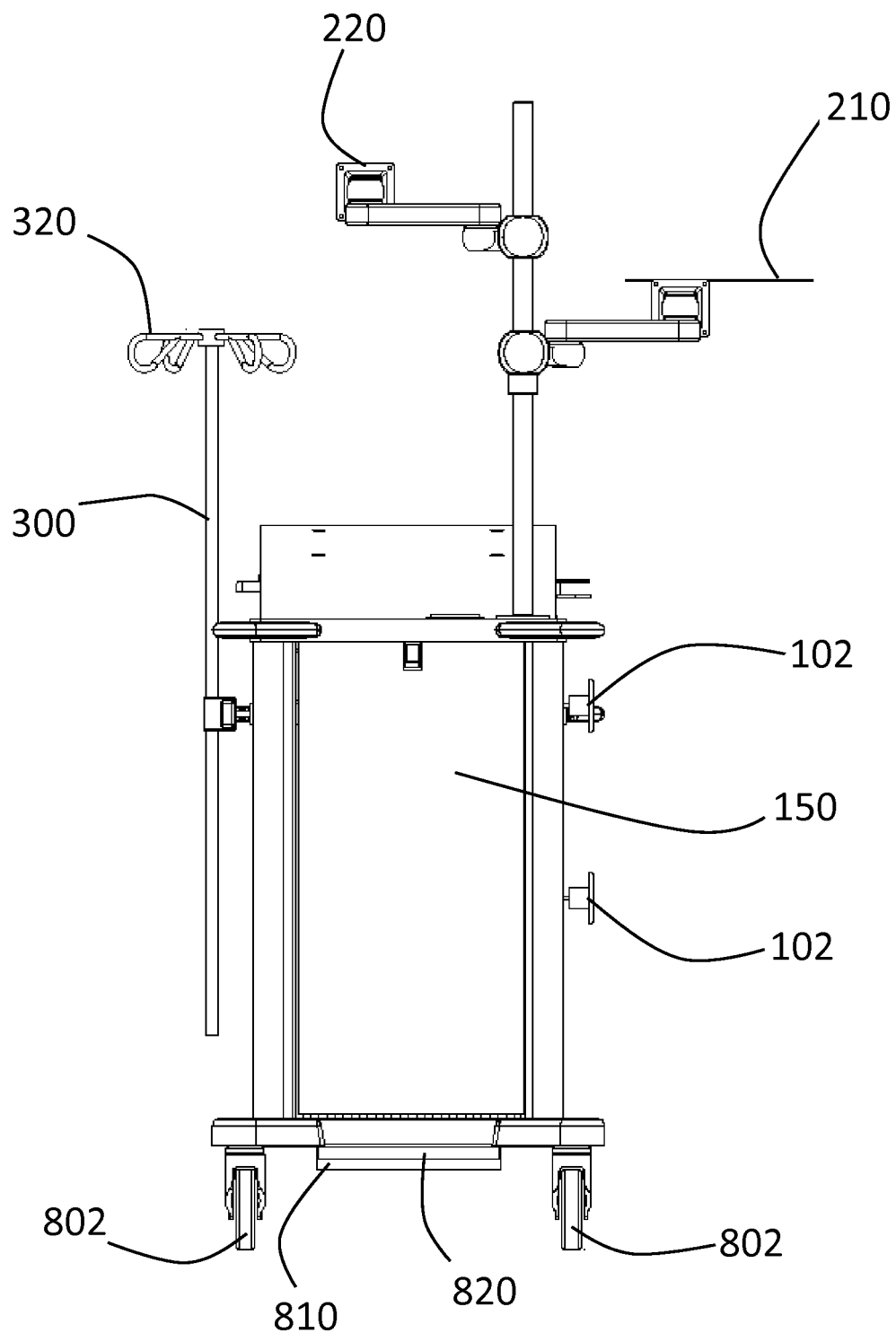
FIG. 4 is a rear view of a medical trolley cart in accordance with a preferred embodiment of the present invention.
Figure 5:
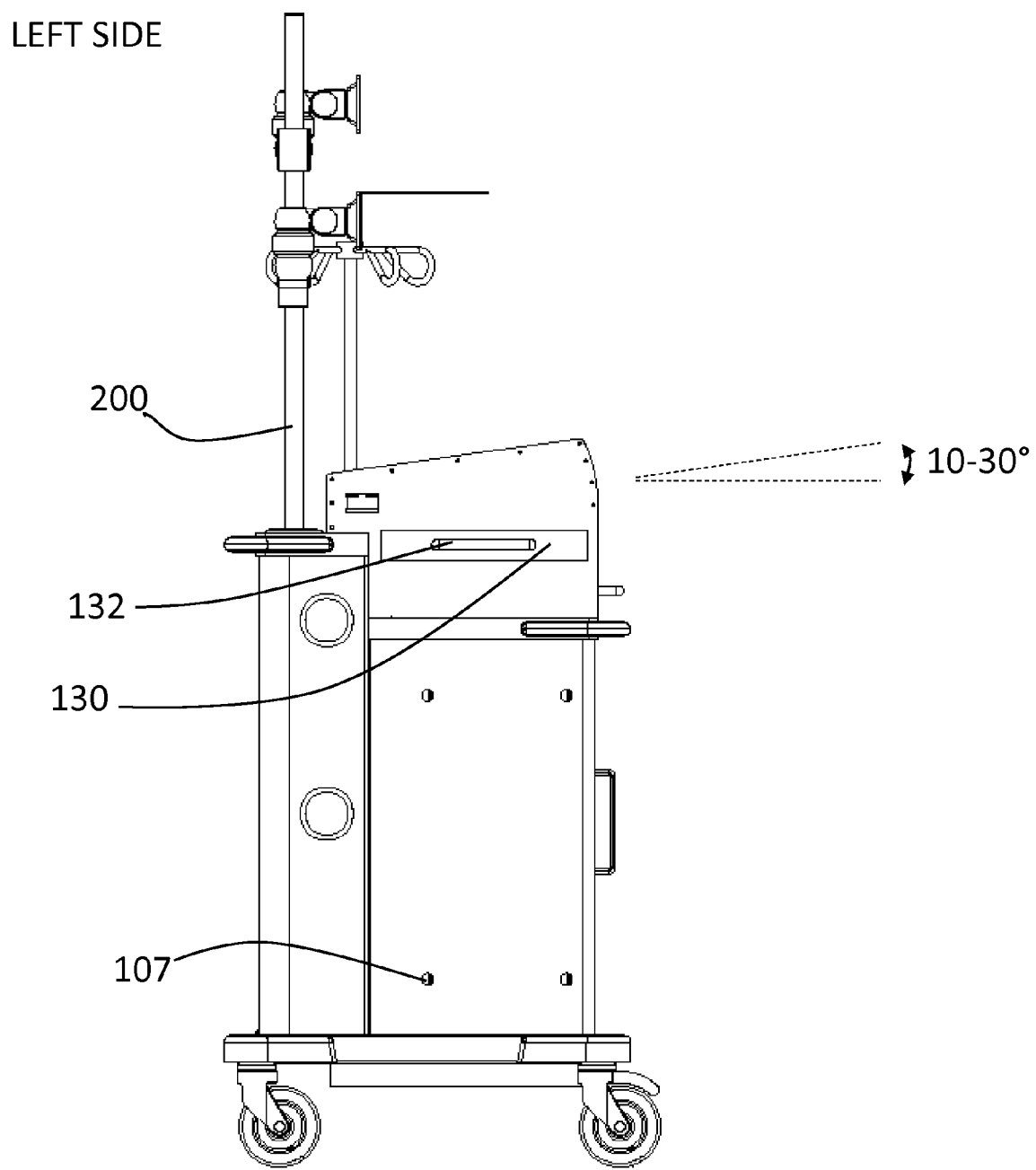
FIG. 5 is a first side view of a medical trolley cart in accordance with a preferred embodiment of the present invention.
Figure 6:
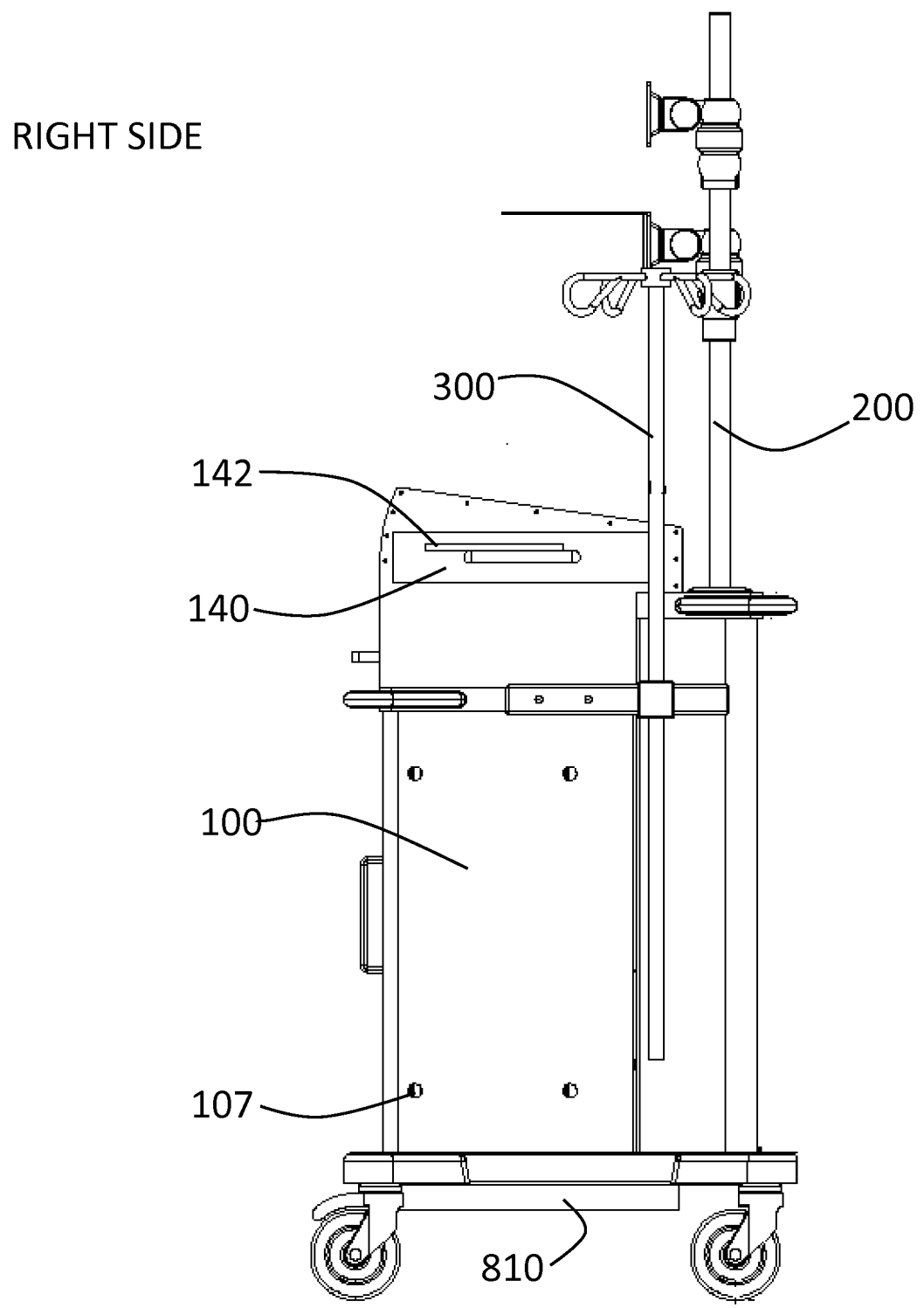
FIG. 6 is a second side view of a medical trolley cart in accordance with a preferred embodiment of the present invention.
Figure 7:
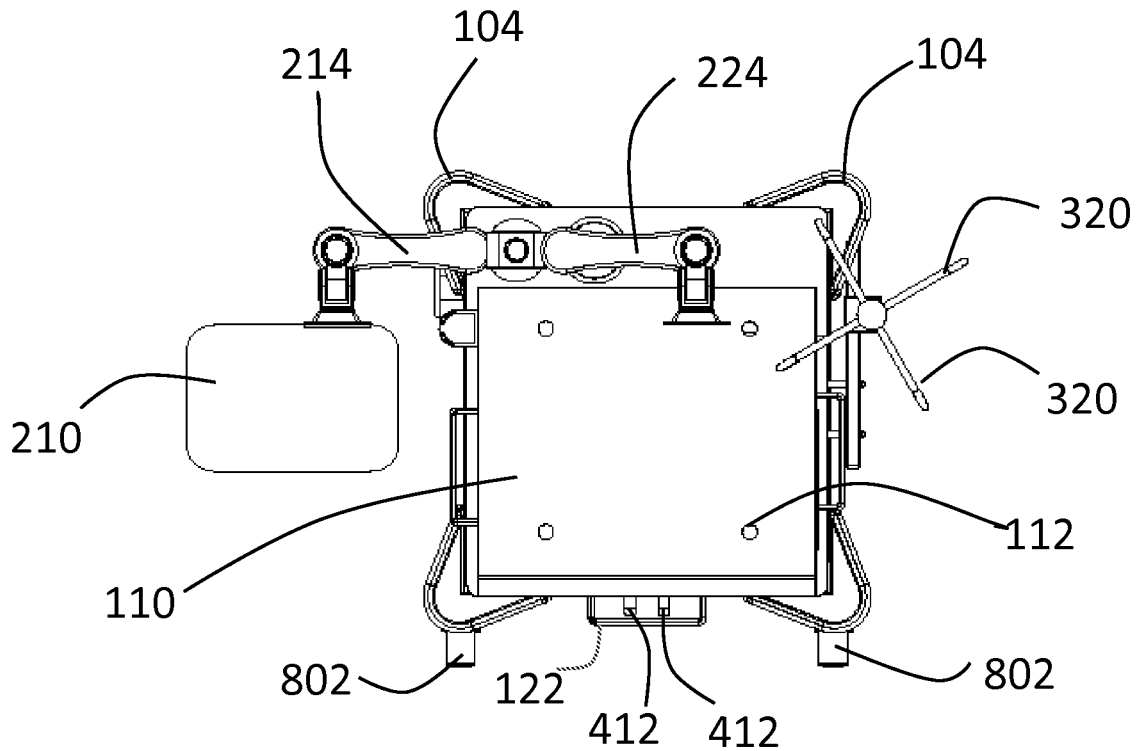
FIG. 7 is a top view of a medical trolley cart in accordance with a preferred embodiment of the present invention.

A preferred embodiment of a medical trolley cart in accordance with the present invention is shown in FIGS. 1-13 with all of its compartments, drawers and workstations in closed positions. The medical trolley cart has a main housing 100 having a plurality of handles 104 for using by operating room personally in moving the cart, attachment members 106, which may be, for example, a bottle holder. The main housing 100 may be formed, for example, from a frame having a plurality of panels connected to the frame or to one another by screws 107. The main housing has a plurality of wheels 802 with mounting members 804. The wheels 802 preferably include locking capability to ensure that the cart can remain in a stationary position. The main housing has on its front a drawer 120 having a handle 122 and a pair of doors 410 having handles 412. The doors 410 are flexible in form such that they can slide back into a compartment in the main housing 100, for example, on rollers, slides or other known means.

A first side the main housing 100 has a plurality of protruding elements 102, for example, for hanging cords, cables or other items on the cart, and a drawer 130 having a handle 132. Near the rear of that first side there is a post 200 extending vertically. Party-way vertically up the post 200 is a hinge connector 212 holding an arm 214 that in turn is connected to a platform 210 via hinge 216. The hinges or rotatable mounting members 212 and 216 may be of any known type and allow the platform to be positioned in any number of positions. The hinge 212 is movable vertically up and down the post 200 and can be removably locked or fixed at any height along the post 200. The platform 210 may be used in an operating room, for example, for holding instruments or a notebook or a laptop computer. Also on the post 200 is a second slidable hinge 222 connected to an arm 224 with a bracket 220 connected thereto by hinge or rotatable mounting member 226 for holding, for example, a monitor.

The other side of the cart has a workstation 140 having a handle 143 and a pull-out extension 142. The work station 140 and extension 142 may be used, for example, for holding a laptop computer or other device. Also on the second side is a post 300 mounted via mounting block or bracket 330 and with, for example, a plurality of IV hooks 320 mounted to a rotatable member 310. On the rear of the trolley is a gas canister compartment 150 having a latch 152 for holding the compartment in a closed position and a hinge or hinges 154. Near the rear of the top of the cart is an opening 108 for holding any cylindrical item or which may be fitted with an insert to hold another post similar to post 200.

The top of the trolley cart has a mounting surface 110 with mounting holes or elements 112. The mounting surface is angled away from the front of the cart by 10-30 degrees. Equipment such as an electrosurgical generator or argon plasma coagulation unit (not shown) may be mounted to the mounting surface 110 using bolts, legs or other mounting members on the generator or other equipment in holes 112. The 10-30° angle of the mounting surface 110 makes the screens and controls of the mounted equipment more visible to the operating room personnel.

Figure 8:
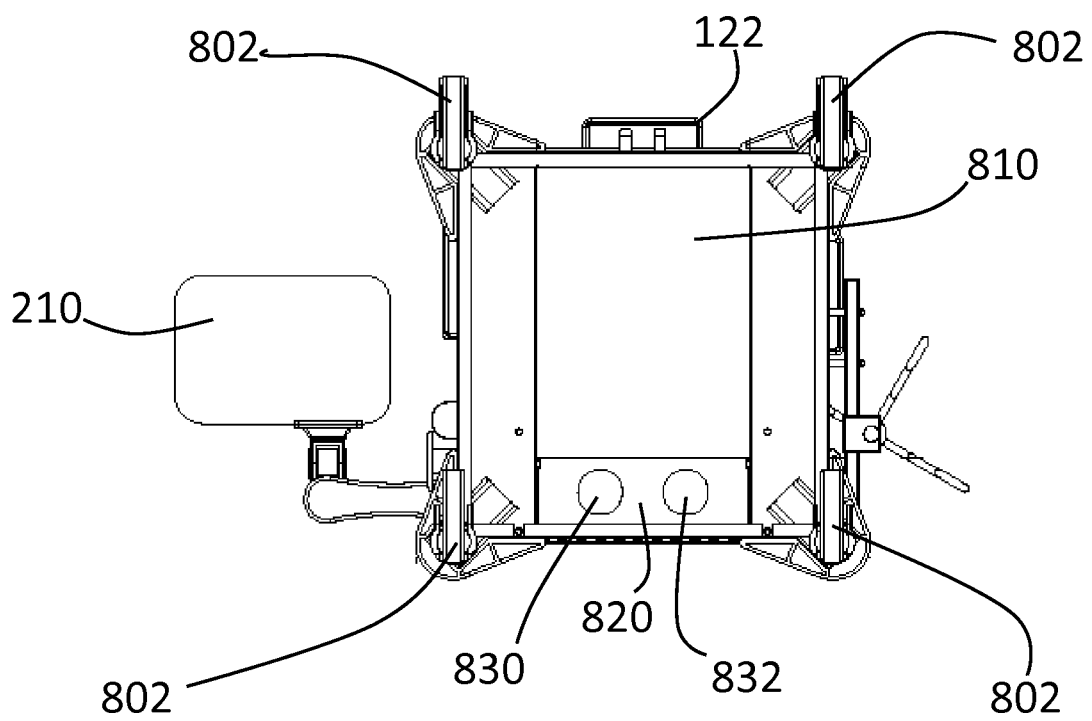
FIG. 8 is a bottom view of a medical trolley cart in accordance with a preferred embodiment of the present invention.
Figure 9:
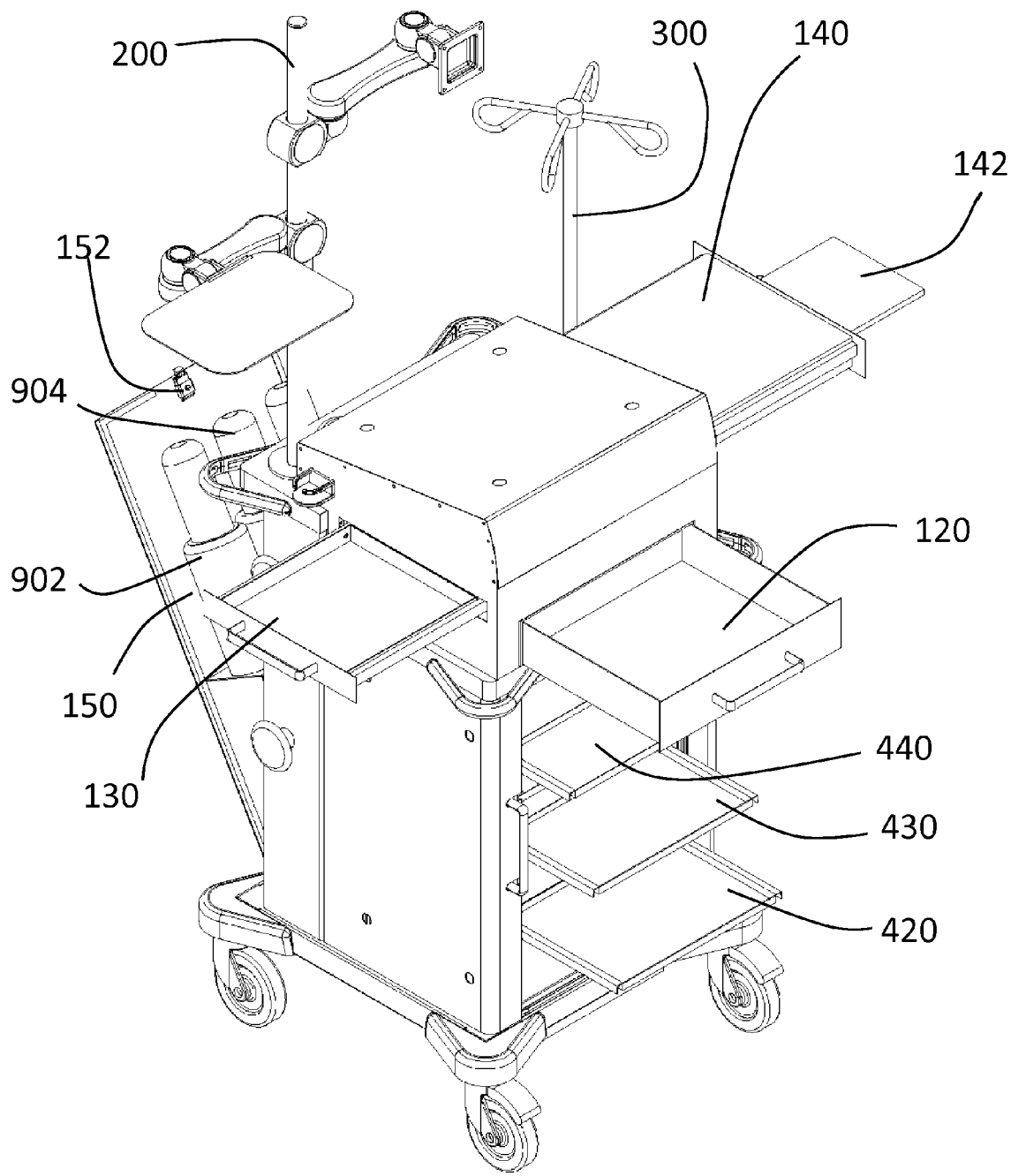
FIG. 9 is a front perspective view of a medical trolley cart in accordance with a preferred embodiment of the present invention with its compartments, drawers and shelves in open positions.

On the bottom of the cart, as shown in FIG. 8, there is a winder 810 for storing an extension cord, and electrical housing unit 820 and a plurality of openings 830, 832 for allowing cords or hoses to extend out of the interior of the trolley.

Figure 10:
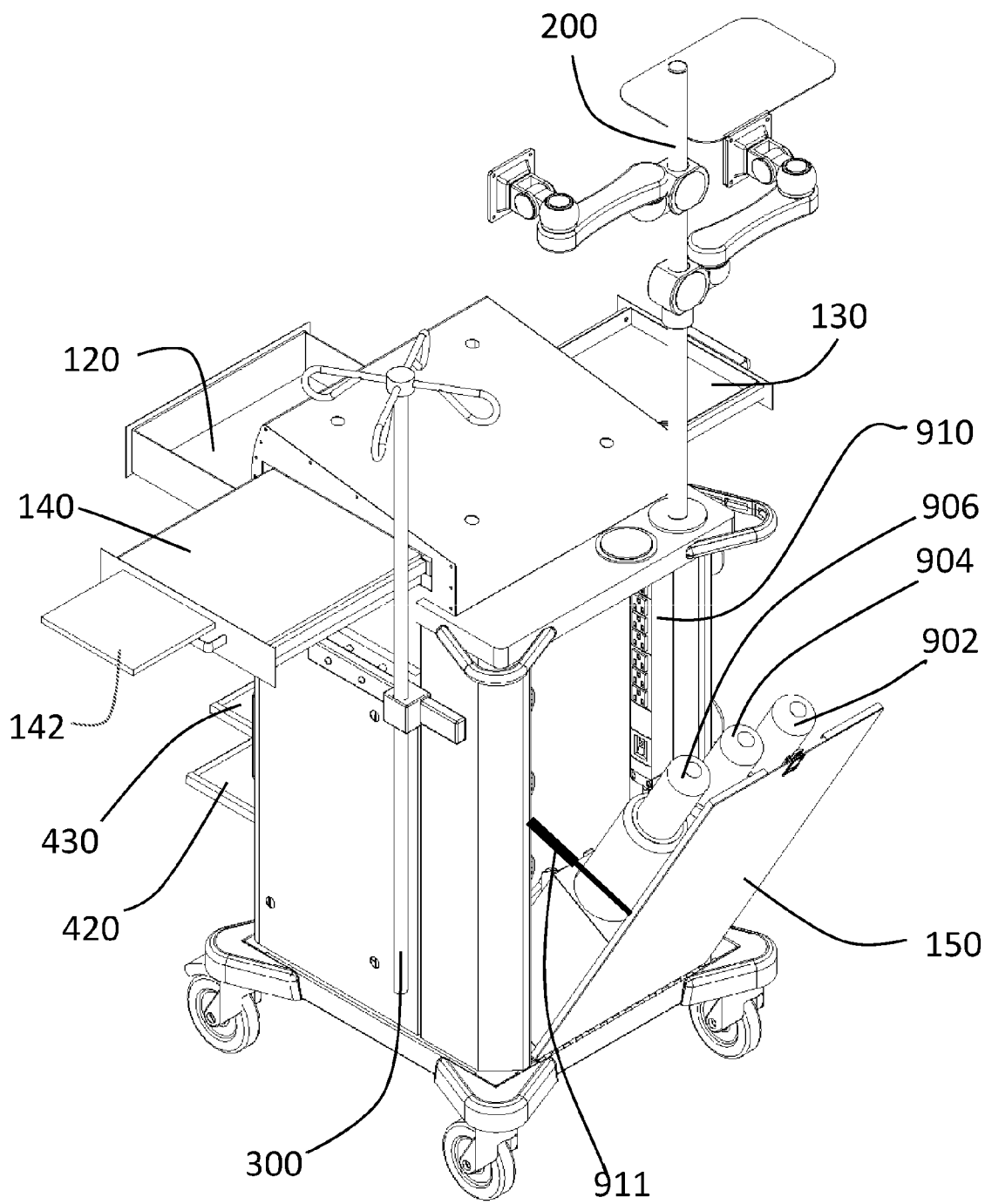
FIG. 10 is a rear perspective view of a medical trolley cart in accordance with a preferred embodiment of the present invention with its compartments, drawers and shelves in open positions.
Figure 11:
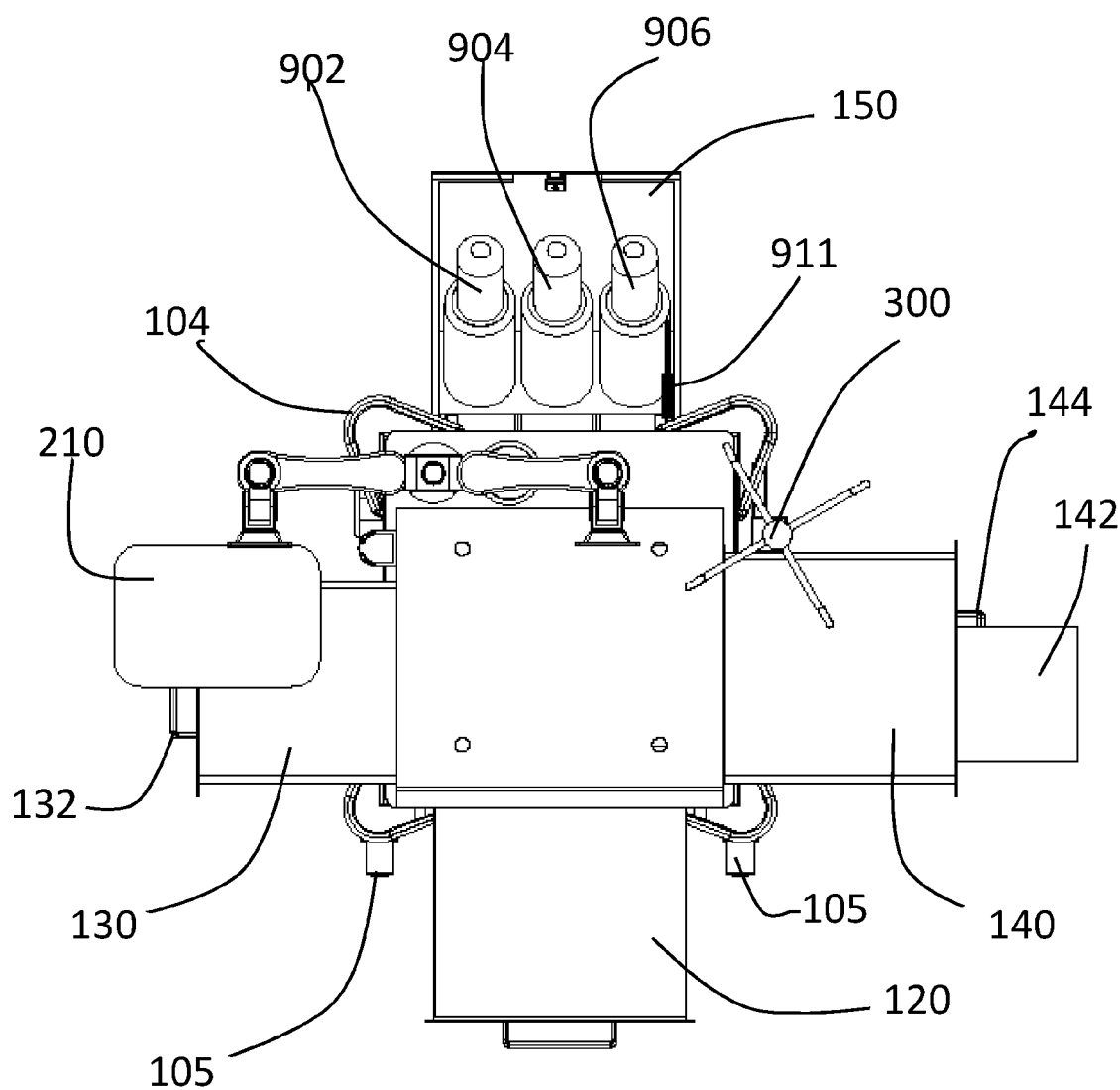
FIG. 11 is a top view of a medical trolley cart in accordance with a preferred embodiment of the present invention with its compartments, drawers and shelves in open positions.
Figure 12:
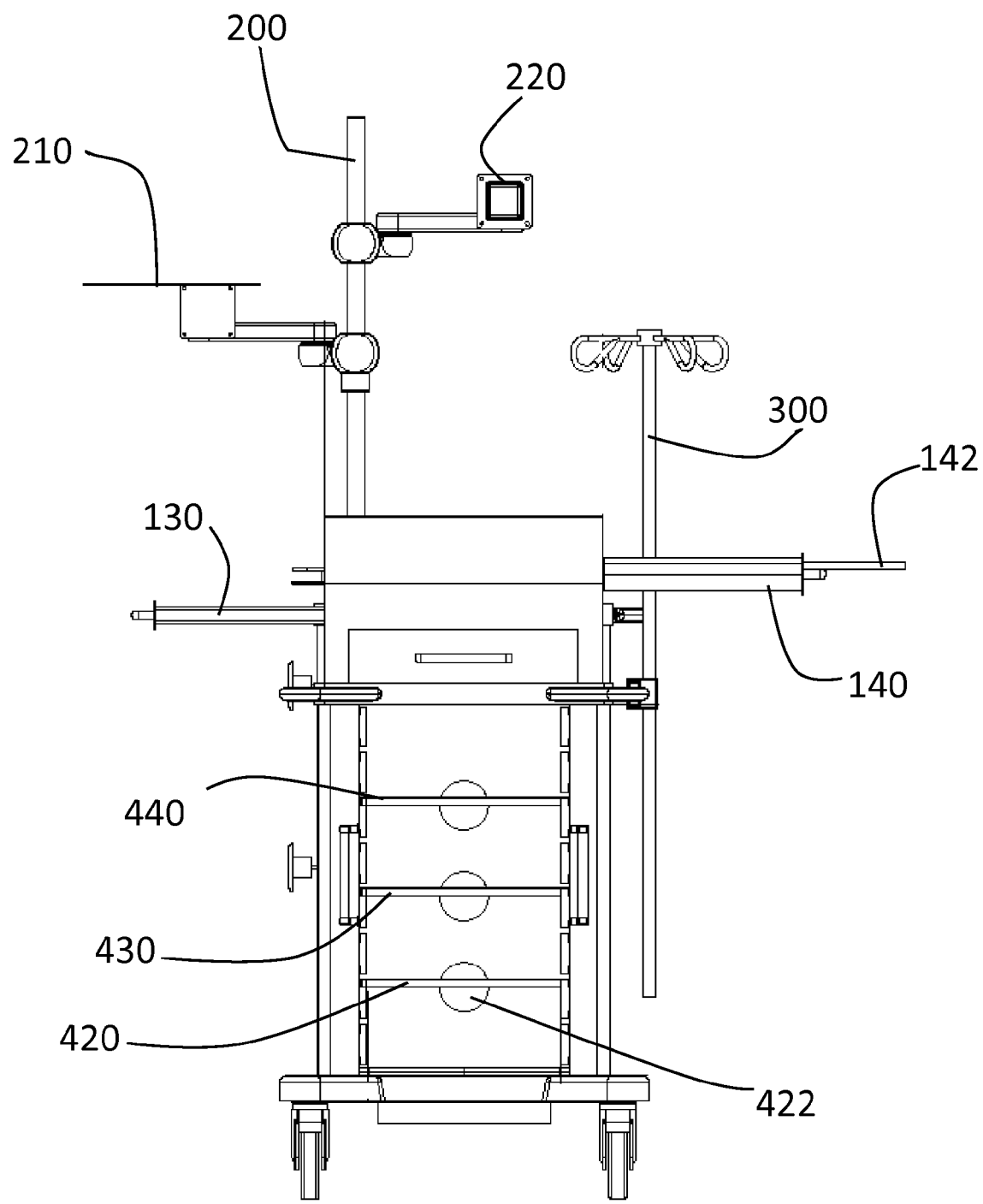
FIG. 12 is a front view of a medical trolley cart in accordance with a preferred embodiment of the present invention with its compartments, drawers and shelves in open positions.
Figure 13:
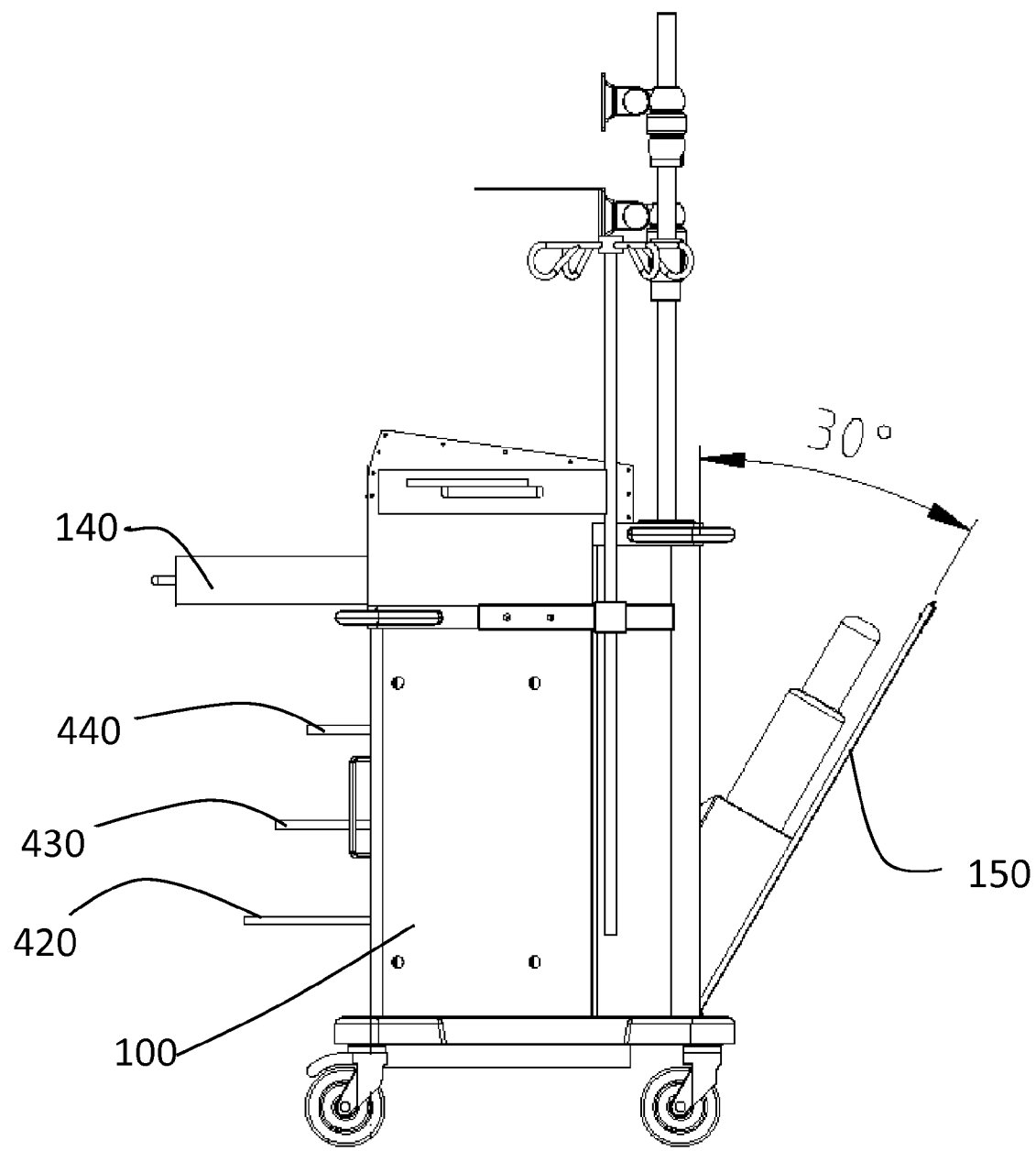
FIG. 13 is a side view of a medical trolley cart in accordance with a preferred embodiment of the present invention with its compartments, drawers and shelves in open positions.

The trolley cart is further shown in FIGS. 9-13 with all compartments, drawers, shelves and work stations in open positions. The compartment accessible from the front the cart has a plurality of sliding shelves, 420, 430, 440. While three shelves are shown in this embodiment, fewer or more shelves also are possible. Additionally, the shelves 420, 430, 440 may slide out as shown in the figures or may be fixed within the trolley cart. Further, there may be openings or holes 422 in the rear of the compartment. As shown in FIGS. 10 and 13, the gas compartment 150 opens only a limited amount such as 30 degrees. While a limitation at 30 degrees is shown in the preferred embodiment, other angles, such as in the range of 15-40 degrees, are possible depending on the size and type of gas tanks to be held within the cart. The limitation range of opening of the gas compartments keeps the cart balanced so the heavy weight of full gas tanks or canisters does not tip the cart over. The limitation of the opening of the compartment may be achieved by the hinge 154, a stop, or by any other known means. Additionally, means for assisting the opening and closing of the gas compartment, such as a gas piston or hydraulic arm 911 may be used and may provide a limitation on the maximum angle to which the compartment may open. The compartment includes tank holding member 156 with a plurality of openings, sleeves, straps bolts, or other means for holding gas tanks 902, 904, 906. While three gas tanks 902, 904, 906, are shown, other arrangements with fewer or more gas tanks may be used with the invention. The gas compartment additionally may include one or more vents (not shown). Additionally within the gas compartment or within the front compartment is a surge protector 910 into which a plurality of electrical components, such as an electrosurgical generator, argon plasma unit, or laptop may be plugged in.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A medical trolley cart comprising:
a main housing having a front interior chamber and a rear interior chamber said front and rear interior chambers being separated by a rear wall of said front interior chamber, said housing having a front, back, first side, second side, top and bottom, said top of said housing being fixed in an angled position from front to back by 10-30 degrees, wherein and rear wall of said front interior chamber has a plurality of holes for providing ventilation between said front interior chamber and said rear interior chamber;
a front door on the front of said main housing for accessing said front interior chamber; and
a rear door on the rear of said main housing for accessing said rear interior chamber, said rear door having a hinge around which the door is opened, a latch for holding the rear door in a closed position, and a stop means for limiting said rear door to opening to a maximum point at which the rear door forms an angle of 15-40 degrees with the main housing.

2. A medical trolley cart according to claim 1 wherein said rear door opens to a maximum angle of 30 degrees.

3. A medical trolley according to claim 1 further comprising a drawer in said first side of said main housing.

4. A medical trolley according to claim 1 further comprising a cable winder connected to said bottom of said main housing.

5. A medical trolley according to claim 1, further comprising a plurality of locking wheels connecting to the bottom of said main housing.

6. A medical trolley cart according to claim 1 further comprising a vertical post connected to said main housing.

7. A medical trolley cart according to claim 6, further comprising:
- a slidable connecting hinge mounted on said vertical post; and
- a support arm connected to said slidable connecting hinge.

8. A medical trolley cart according to claim 7, further comprising a monitor mounting bracket connected to said support arm.

9. A medical trolley cart according to claim 7 further comprising a platform connected to said support arm by rotating mounting member.

10. A medical trolley cart comprising:
- a main housing having an interior chamber, said housing having a front, back, first side, second side, top and bottom, said top of said housing being angled from front to back by 10-30 degrees;
- a front door on the front of said main housing for accessing said interior chamber; and
- a rear door on the rear of said main housing for accessing a rear portion of said interior chamber, said rear door having a hinge around which the door is opened, a latch for holding the rear door in a closed position, and a stop means for limiting said rear door to opening to a maximum point at which the rear door forms an angle of 15-40 degrees with the main housing;

wherein said rear door has a gas piston attached thereto.

11. A medical trolley according to claim 1, further comprising a work station in said second side of said main housing.

12. A medical trolley cart according to claim 1, further comprising a gas tank holding member connected to an interior of said rear door.

\* \* \* \* \*